United States Patent [19]

Luo

[11] 4,259,486

[45] Mar. 31, 1981

[54] METHOD FOR THE AMINOALKYLATION OF PHENOL

[75] Inventor: Tatao Luo, Hamilton Square, N.J.

[73] Assignee: American Cyanamid Company, Stamford, Conn.

[21] Appl. No.: 118,275

[22] Filed: Feb. 4, 1980

[51] Int. Cl.$^3$ .......................................... C07D 295/08
[52] U.S. Cl. ..................................... 544/173; 568/790
[58] Field of Search ........................... 544/173; 568/790

[56] References Cited

U.S. PATENT DOCUMENTS

| | | | |
|---|---|---|---|
| 2,246,726 | 6/1941 | Schirm | 568/790 |
| 2,435,087 | 1/1948 | Luten et al. | 568/790 |
| 3,051,762 | 8/1962 | Stroh et al. | 568/790 |

*Primary Examiner*—Henry R. Jiles
*Assistant Examiner*—R. W. Ramsuer
*Attorney, Agent, or Firm*—H. G. Jackson

[57] ABSTRACT

The present invention relates to the aminoalkylation of phenol with 4-(alkenyl)morpholines, preferably in the presence of lithium chloride. The present invention further relates to the p-(morpholinoalkyl)phenols obtained by the above method.

3 Claims, No Drawings

METHOD FOR THE AMINOALKYLATION OF PHENOL

SUMMARY OF THE INVENTION

The present invention relates to a method for for the preparation of a compound of formula (I)

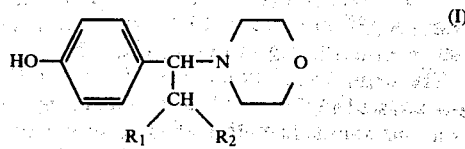

wherein $R_1$ and $R_2$ are hydrogen or $C_1-C_2$ alkyl, straight chain or branched, and is preferably isopropyl. Compounds of formula (I), especially wherein $R_1$ is isopropyl, are useful and valuable intermediates for the preparation of compounds of formula (II)

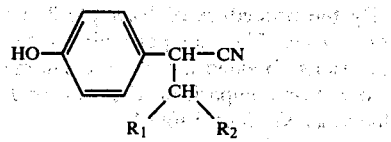

wherein $R_1$ and $R_2$ are as hereinabove defined, and are preferably both methyl. The compounds represented by formula (II) have been disclosed as useful and valuable intermediates for the preparation of pyrethroid type insecticides and ixodicides, in South African Pat. No. 77/5598, issued 3/7/79 and in Belgium Pat. No. 183695, issued 12/21/77, both of which are incorporated herein by way of reference.

The compounds of the invention as represented by formula (I), may be conveniently prepared by the following reaction sequence:

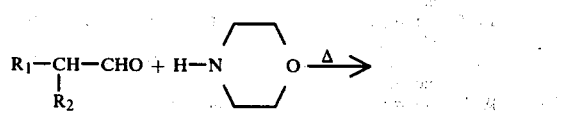

(III)

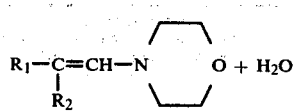

(IV)
and

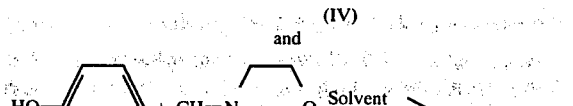

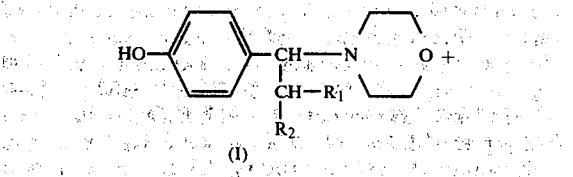

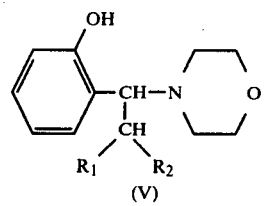

(V)

wherein $R_1$ and $R_2$ are hydrogen or $C_1-C_2$ alkyl, and are preferably both methyl.

Thus, an aldehyde of formula (III) is added with stirring to morpholine in amounts in excess over theory, and after the initial exotherm subsides, the reaction mixture is heated to a sufficiently high temperature to facilitate the removal of water from the reaction mixture by azeotroping same as it is formed in the course of the reaction. The product (IV) thus obtained may be purified, if so desired, by standard laboratory procedures such as vacuum distillation, and the like. The thus obtained enamine of formula (IV) is then reacted with phenol used in 10–20% molar excess over theory, neat or in the presence of a solvent such as isopropyl alcohol, acetonitrile, toluene and the like, preferably isopropyl alcohol, and in the temperature range of from about 20° C. to about 90° C., and preferably 40° C. to 60° C. for a period of time from about 20 hours to about 240 hours or until the reaction is essentially complete. In the course of this reaction, as illustrated above, the ortho isomer (V) is also obtained in addition to the desired para isomer (I). Advantageously, we find, that the formation of the desired compound of formula (I) may be increased significantly by adding lithium chloride to the above reaction mixture in molar amounts equal to that of the phenol used.

The identity of compounds (I) and (V) is established by comparing the samples obtained by the above route to authentic samples prepared by unequivocal routes as shown below:

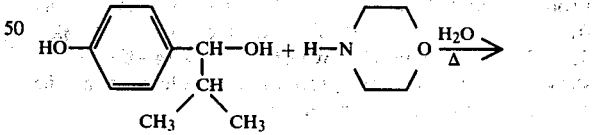

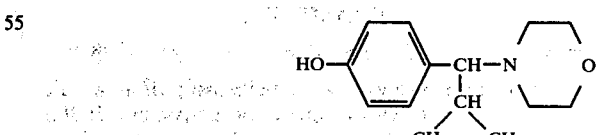

(I)
and

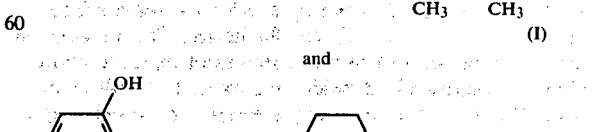

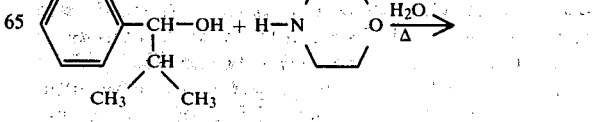

-continued

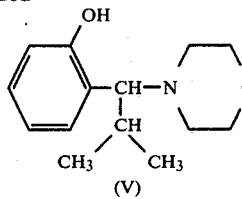

As stated above, the compounds of formula (I) are valuable intermediates for the preparation of formula (II) compounds, and these in turn are disclosed in the aforementioned patents as key intermediates for the preparation of insecticidal and ixodicidal pyrethroids.

Advantageously, a compound of formula (I) is heated with an excess of an alkali metal cyanide in the presence of water to obtain a compound of formula (II) as shown below:

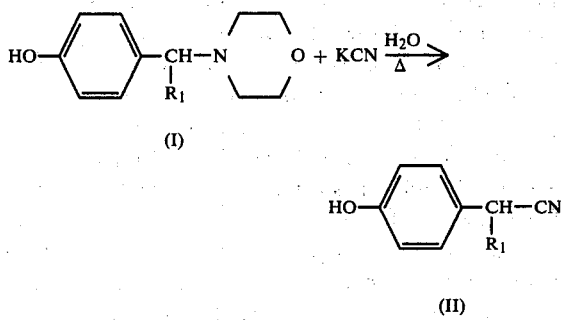

wherein $R_1$ is as hereinabove defined.

The present invention is further illustrated by the following non-limiting examples.

EXAMPLE 1

Preparation of 4-(2-methylpropenyl)morpholine

Isobutyraldehyde (19.4 g; 0.27 mol) is added slowly with stirring to morpholine (21.75 g; 0.25 mol). The ensuing reaction is exothermic. On completion of the addition the reaction mixture is stirred and heated at reflux for 5 hours while water (4.1 ml) is being azeotroped out of it. The reaction mixture is then vacuum distilled. A fraction collected at 64°–67° C. and 13 mm Hg weighs 15.6 g and consists of 90% by weight of title product and 10% by weight of morpholine. A second fraction collected at 67°–67.5° C. and 13 mm Hg (lit. 56°–57° C.; 11 mm Hg) weighs 16.2 g (46%) and is shown to be pure title product by nuclear magnetic resonance (nmr) and infrared (ir).

EXAMPLE 2

Preparation of 4-(2-methyl-1-morpholinopropyl)phenol

A mixture of phenol (34.0 g; 0.36 mol), lithium chloride (15.1 g; 0.36 mol), 4-(2-methylpropenyl)morpholine (42.3 g; 0.30 mol) and isopropyl alcohol (30 ml) is stirred and heated at 55°–57° C. for 88 hours. The reaction mixture is then cooled to room temperature, taken up in 250 ml 5% sodium hydroxide, and extracted with ether (3×, 100 ml). The ethereal extracts are combined, washed with water, dried over magnesium sulfate and concentrated to yield 21.5 g of fraction (I). Analysis by n.m.r. indicates this fraction (I) to contain 13.7 g (19%) of 2-(2-methyl-1-morpholinopropyl)phenol (the ortho isomer of the title product), 2.5 g of 4-(2-methylpropenyl)morpholine, 4.9 g of an unknown and 0.4 g of isopropyl alcohol.

The above aqueous (alkaline) solution is cooled to 0°–5° C. and acidified to pH 1 with 6 N hydrochloric acid while maintaining the temperature of the solution below 15° C. The acidified solution is extracted with ether (3×, 100 ml), the ethereal extracts are combined, washed with water (30 ml) and concentrated to yield 19.4 g of fraction (II). Analysis by n.m.r. indicates this fraction (II) to contain 15.9 g of phenol, 2.0 g of an unknown and 1.5 g of isopropyl alcohol.

The aqueous solution is cooled again to 0°–5° C., its pH adjusted to 7–8 with 50% sodium hydroxide, the solution saturated with sodium chloride and then extracted with chloroform (4×, 100 ml). The chloroform extracts are combined, dried over magnesium sulfate and concentrated to yield 29.4 g of fraction (III). Analysis by n.m.r. indicates this fraction (III) to contain 28.1 g (40%) of title product, and 1.3 g (5%) of morpholine.

EXAMPLE 3

Preparation of 4-(2-methyl-1-morpholinopropyl)phenol

By the procedure of Example 2, a number of reactions are run. The data pertaining to these reactions and the results obtained thereby are summarized in Table I below. For comparison, the data of Example 2 is included as No. 8 of Table I.

TABLE I

Reaction of phenol and 4-(2-methylpropenyl)morpholine in a 1.25:1.0 molar ratio to yield 4-(2-methyl-1-morpholinopropyl)phenol

| | | Reaction | | | Component isolated from reaction mixture in wt % | | |
|---|---|---|---|---|---|---|---|
| No | Inorganic Salt | Solvent | Temperature °C. | time (h) | a | b | c |
| 1 | — | — | 45–50 | 96 | 14 | 13 | 14 |
| 2 | — | — | 95–100 | 24 | 6 | 14 | 38 |
| 3 | LiCl | toluene | 20–25 | 240 | 3 | 27 | 8 |
| 4 | LiCl | toluene | 65–70 | 96 | — | 21 | 32 |
| 5 | LiCl | acetonitrile | 45–50 | 18 | 14 | 18 | 4 |
| 6 | LiCl | acetonitrile | 85–90 | 22 | — | 19 | 21 |
| 7 | LiCl | isopropyl alcohol | 45–50 | 66 | 9 | 36 | 10 |
| 8 | LiCl | isopropyl alcohol | 55–57 | 88 | 6 | 40 | 19 |
| 9 | NaCl | isopropyl alcohol | 65–75 | 144 | 11 | 7 | 22 |
| 10 | K Cl | isopropyl alcohol | 65–75 | 144 | 14 | 8 | 19 |
| 11 | $MgCl_2$ | toluene | 45–50 | 48 | ~10 | <5 | <5 | a = 4-(2-methylpropenyl)morpholine
b = 4-(2-methyl-1-morpholinopropyl)phenol
c = 2-(2-methyl-1-morpholinopropyl)phenol

EXAMPLE 4

Preparation of 4-(2-methyl-1-morpholinopropyl)phenol

A mixture of 4-hydroxy-α-isopropylbenzyl alcohol (1.0 g; 0.006 mol) morpholine (1.3 g; 0.015 mol) and water (1.3 ml) is refluxed under a nitrogen atmosphere for 23 hours, and then poured into water (~20 ml). The aqueous solution is extracted with 30 ml of ether, the ethereal solution dried over magnesium sulfate, and concentrated to give 0.97 g of crude product (69% of theory). Recrystallization of the crude product from methylene chloride affords pure title compound (490 mg 35%): mp 142°–143° C.; IR (Nujol) 3300 (s), 2940 (s), 1610 (m), 1595 (m) cm$^{-1}$; NMR (CDCl$_3$) δ0.75 and 0.92 (a pair of d, J=7 Hz, 6 H, two methyls), 1.8–2.4 (m, 1 H, isopropyl methine proton), 2.3–2.5 (m, 4 H, two methylene groups adjacent to the nitrogen atom), 2.94 (d, J=8 Hz, 1 H, benzylic proton), 3.6-3.9 (m, 4 H, two methylene groups adjacent to the oxygen atom), 3.9-6.2 (broad s, 1 H, phenoxy proton) and 6.75 and 7.05 ppm (AB quartet, J=8 Hz, 4 H, aromatic). Anal. Calcd for $C_{14}H_{21}NO_2$: C, 71.45; H, 8.95; N, 5.95. Found: C, 71.07; H, 8.64; N, 6.01.

EXAMPLE 5

Preparation of 2-(2-methyl-1-morpholinopropyl)phenol

By the procedure of Example 4, but substituting 2-hydroxy-α-isopropylbenzyl alcohol for the 4-hydroxy isomer, the crude product is obtained in 59% yield which, on recrystallization from hexanes and methylene chloride, affords pure title compound, (23%): mp 73°-77° C.; IR (Nujol) 3400-2200 (broad, intramolecular H-bonding), 1610 (w), 1590 (m); NMR (CDCl$_3$) δ0.8 and 0.9 (a pair of d, J=1 Hz, 6 H, two methyls), 2.0-2.6 (m, 1 H, isopropyl methine proton), 2.5-2.7 (m, 4 H, two methylene groups adjacent to the nitrogen atom), 3.22 (d, J=4 Hz, 1 H, benzylic proton), 3.6-3.9 (m, 4 H, two methylene groups adjacent to the oxygen atom), 6.7-7.35 (m, 4 H, aromatic protons). Anal. Calcd for $C_{14}H_{21}NO_2$: C, 71.45; H, 8.95; N, 5.95. Found: C, 71.36; H, 9.20; N, 5.94.

EXAMPLE 6

Preparation of 2-(4-hydroxyphenyl)-3-methylbutyronitrile

A mixture of 4-(2-methyl-1-morpholinopropyl) phenol (2.35 g; 0.01 mol), potassium cyanide (1.6 g; 0.024 mol) and water (2.5 ml) is heated at 95°-100° C. for 17 hours. The reaction mixture is then cooled down, and added to about 35 ml of 5% sodium hydroxide. The aqueous solution is washed with ether (2×, 20 ml), and then its pH is adjusted to ~2 with 6 N hydrochloric acid. The acidified aqueous solution is extracted with ether (2×, 30 ml), the ethereal extracts are combined, washed with water, dried over magnesium sulfate, and concentrated to afford 1.7 g of title product, a viscous, almost colorless oil.

We claim:

1. A method for the preparation of a compound of formula

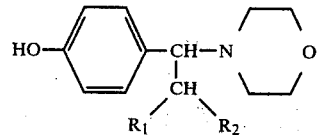

wherein $R_1$ and $R_2$ are hydrogen or $C_1$-$C_2$ alkyl, straight chain or branched, comprising: reacting a compound of formula

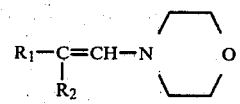

wherein $R_1$ and $R_2$ are as hereinabove defined with phenol used is 10-20% excess over theory in the presence of a solvent selected from isopropyl alcohol, acetonitrile and toluene and in the presence of lithium chloride added in molar amounts equal to that of the phenol used, and in the temperature range of 20° C. to 90° C. for a period of time sufficient to essentially complete the reaction.

2. A method according to claim 1, wherein one mole of 4-(2-methylpropenyl)morpholine is reacted with 1.2 moles of phenol in the presence of isopropyl alcohol and of 1.2 moles of lithium chloride at 55°-57° C. for a period of time sufficient to essentially complete the reaction.

3. A method according to claim 2, wherein the reaction temperature is 45°-50° C.